(12) United States Patent
Gomez et al.

(10) Patent No.: US 8,188,145 B2
(45) Date of Patent: May 29, 2012

(54) SYNTHETIC LACTONE FORMULATIONS AND METHOD OF USE

(75) Inventors: Federico M. Gomez, Boca Raton, FL (US); C. Federico Gomez Garcia-Godoy, Santo Domingo (DO)

(73) Assignee: Magnachem International Laboratories, Inc., Boca Raton, FL (US)

( * ) Notice: Subject to any disclaimer, the term of this patent is extended or adjusted under 35 U.S.C. 154(b) by 915 days.

(21) Appl. No.: 11/108,198

(22) Filed: Apr. 18, 2005

(65) Prior Publication Data
US 2005/0239877 A1    Oct. 27, 2005

Related U.S. Application Data

(63) Continuation-in-part of application No. 10/172,462, filed on Jun. 12, 2002, now Pat. No. 6,900,242.

(60) Provisional application No. 60/565,114, filed on Apr. 23, 2004.

(51) Int. Cl.
*A61K 31/34* (2006.01)
*A61K 31/40* (2006.01)
*C07D 307/00* (2006.01)
*C07D 333/32* (2006.01)
*C07D 207/00* (2006.01)

(52) U.S. Cl. ........ 514/473; 514/472; 514/445; 514/447; 514/424; 514/425; 549/313; 549/295; 549/68; 549/63; 548/543; 548/544; 548/545; 548/546; 548/558

(58) Field of Classification Search ................... 549/313, 549/295, 68, 63; 548/543, 544, 545, 546, 548/558; 514/473, 472, 445, 447, 424, 425, 514/426
See application file for complete search history.

(56) References Cited

U.S. PATENT DOCUMENTS

| | | | |
|---|---|---|---|
| 2,624,723 A | 1/1953 | McGraw et al. | |
| 2,624,732 A | 1/1953 | Hitchings et al. | |
| 3,203,953 A | 8/1965 | Lucas et al. | |
| 3,210,377 A | 10/1965 | Machleidt et al. | |
| 3,993,771 A | 11/1976 | Uematsu et al. | |
| 4,001,425 A | 1/1977 | Price, Jr. et al. | |
| 4,613,613 A | 9/1986 | Oguri et al. | |
| 5,242,945 A | 9/1993 | Caufield et al. | |
| 5,250,735 A | 10/1993 | Wong et al. | |
| 5,281,622 A | 1/1994 | Wong et al. | |
| 5,595,756 A | 1/1997 | Bally et al. | |
| 5,646,164 A | 7/1997 | Tzeng et al. | |
| 5,905,089 A | 5/1999 | Hwang et al. | |
| 5,962,460 A | 10/1999 | Tzeng et al. | |
| 5,977,169 A | 11/1999 | Chrusciel et al. | |
| 5,981,575 A | 11/1999 | Kuhajda | |
| 6,180,651 B1 | 1/2001 | Nicolai et al. | |
| 6,222,048 B1* | 4/2001 | Black et al. | 549/60 |
| 6,232,474 B1 | 5/2001 | Brandenburg et al. | |
| 6,395,724 B1* | 5/2002 | Judice et al. | 514/183 |
| 6,686,390 B2* | 2/2004 | Pal et al. | 514/473 |
| 6,900,242 B2* | 5/2005 | Terrero | 514/473 |
| 7,323,495 B2 | 1/2008 | Terrero | |
| 2005/0101663 A1 | 5/2005 | Terrero et al. | |
| 2005/0209316 A1 | 9/2005 | Terrero | |
| 2008/0125484 A1 | 5/2008 | Terrero | |

FOREIGN PATENT DOCUMENTS

| | | |
|---|---|---|
| EP | 0 534 907 | 3/1993 |
| EP | 0 712 843 | 11/1999 |
| JP | 51-125722 | 11/1976 |
| JP | 54-084564 | 7/1979 |
| JP | 56-128776 | 10/1981 |
| JP | 56128776 | 10/1981 |
| JP | 58-099413 | 6/1983 |
| JP | 62-026221 | 2/1987 |
| JP | 64-016776 | 1/1989 |
| JP | 01-163175 | 6/1989 |
| JP | 2002-37797 A2 | 2/2002 |
| WO | WO 96/29392 | 9/1996 |
| WO | WO 97/18806 | 5/1997 |
| WO | WO 97/28147 | 8/1997 |
| WO | WO 98/40078 | 9/1998 |
| WO | WO 98/43966 | 10/1998 |
| WO | WO 99/53915 | 10/1999 |
| WO | WO 01/39720 | 6/2001 |
| WO | WO 01/39720 | 9/2001 |
| WO | WO 01/64913 | 9/2001 |
| WO | WO 02/064160 | 8/2002 |
| WO | WO 02/100854 | 12/2002 |
| WO | WO/2004/041217 | 5/2004 |

OTHER PUBLICATIONS

Chen, et al., "α-Methylene-γ-butyrolactones: synthesis and vasorelaxing activity assay of coumarin, naphthalene, and quinolone derivatives", *Chem. Pharm. Bull.*, 46(6):962-965 (1998).

Fuchino, et al., "New sesquiterpene lactones from *Elephantopus mollis* and their leishmanicidal activities", *Planta Med*, 67:647-653 (2001).

Grigg, et al., "X=Y-ZH Systems as potential 1,3-dipoles part 35. Generation of nitrones from oximes. Class 3 processes. Tandem intramolecular Michael addition (1,3-azaprotio cyclotransfer)-intermolecular 1,3-dipolar cycloaddition reactions.[1,2]", *Tetrahedron*, 48(33):6929-6952 (1992).

Huang, et al., "Synthetic and cytotoxic studies of α-methylene-γ-butyrolactone bearing pyrimidines", *Kaohsiung J. Med. Sci.* 9:707-711 (1993).

Kuhajda, et al., "Synthesis and antitumor activity of an inhibitor of fatty acid synthase," *Proc. Natl. Acad. Sci. USA*, 97(7):3450-3454 (2000).

(Continued)

*Primary Examiner* — Andrew D Kosar
*Assistant Examiner* — Raymond Covington
(74) *Attorney, Agent, or Firm* — Pabst Patent Group LLP

(57) ABSTRACT

Natural and synthetic compounds having a lactone structure methods for alleviation of pain, especially pain associated with disorders such as melanoma, leukemia, breast cancer, lung cancer, ovarian cancer, colon cancer, esophagus cancer, liver cancer, and lymphatic cancer. Initial studies have shown that patients can be taken off of morphine when the preferred alpha-methylene-gamma-butyrolactone is administered in a dosage of between 60 and 120 mg/day intramuscularly.

10 Claims, No Drawings

OTHER PUBLICATIONS

Lee, et al., "Sesquiterpene antitumor agents: inhibitors of cellular metabolism", *Science*, 196:533-535 (1977).
Lee, et al., "Synthesis and anticancer evaluation of certain α-methylene-γ-(4-substituted phenyl)-g-butyrolactone bearing thymine, uracil, and 5-bromouracil", *Bioorg. &Med. Chem.*, 9:241-244 (1999).
Maria, et al., "Gastric anti-ulcer activity of several α,β-unsaturated carbonyl compounds in rats", *Biol. Pharm. Bull.*, 23(5):555-557 (2000).
Panda, et al., "Mechanism of action of alpha-methylene-gamma-lactone derivatives of substituted nucleic acid bases in tumour cells", *Chemotherapy*, 35:174-180 (1989).
Rodriguez, et al., "Biological activities of sesquiterpene lactones", *Phytochemistry*, 15:1573-1580 (1976).
Sanyal, et al., "New α-methylene-γ-lactone derivatives of substituted nucleic acid bases as potential anticancer agents", *J. Med. Chem.*, 29(5):595-599 (1986).
Schlewer, et al., "Synthesis of α-methylene-γ-butyrolactones: a structure-activity relationship study of their allergenic power", *J. Med. Chem.*, 23:1031-1038 (1980).
Spring, et al., "Annuithrin, a new biologically active germacranolide from *Helianthus annuus*", *Phytochemistry*, 20(8):1883-1885 (1981).
Willuhn, "*Arnica* flowers: pharmacology, toxicology, and analysis of the sesquiterpene lactones—their main active substance," in *Phytomedicines of Europe: Chemistry and Biological Activity* (Lawson, et al, eds.) Washington DC American Chemical Society, pp. 118-132 (1997).
Baldwin, et al., 5-endo-Trigonal reactions: a disfavoured ring closure, *J. Chem Soc. Chem Comm.*, 18:736-38 (1976).
Cassady, et al., "Potential antitumor agents. Synthesis, reactivity, and cytoxicity of alpha-methylene carbonyl compounds", *J Med Chem.*, 21(8):815-9 (1978).
Chester, et al., "α-methylene butyrolactone from *Erythronium americanum*," *J. Am. Chem. Soc.*, 68:2332-4 (1946).
Hoffmann and Rabe, "Synthese und biologische activitat von α-methylen-γ-butyrolactonen," *Angewandte Chemie*, 97(2):96-112 (1985).
Howie, et al., "Synthesis of alkyl-substituted α,β-unsaturated γ-lactones as potential antitumor agents," *J Med Chem.*, 17(8):840-3 (1974).
Ingolfsdottir, et al., In vitro susceptibility of *Helicobacter pylori* to protolichesterinic acid from the lichen *Cetraria islandica Antimicrob Agents Chemother*. 1997 41(1):215-7 (1997).
Lenz, et al., "A test battery of bacterial toxicity assays and comparison of $LD_{50}$ values," *Toxicity Assessment*, 4(1):43-52 (1989).
Park, et al., "Anti-helicobacter pylori effect of costunolide isolated from the stem bark of *Magnolia sieboldii*," *Arch. Parm. Res.*, 20(3):275-279 (1997).
Prestera, et al., "Chemical and molecular regulation of enzymes that detoxify carcinogens", *Proc Natl Acad Sci U S A.*, 90(7):2965-9 (1993).
Schuster, et al., "Sesquiterpene lactones from *Koanophyllon albicaule*", *Pytochemistry*, 31(9):3143-6 (1992).
Sussmuth, et al., "Effects of test conditions and interfering factors on sensitivity of bacterial tests based on inhibition of growth and motility," *Environmental Toxicology and Water Quality*, 7(3):257-74 (1992).
Tschesche, et al, "Uber die antibiotisch wirksamen substanzen de tulpe *Tulipa gesneriana*," *Tetrahedron Letters*, 6:701-6 (1968).
Vilella, et al., "Inhibitors of farnesylation of Ras from a microbial natural products screening program," *J Ind Microbiol Biotechnol.*, 25(6):315-327 (2000).
Adam, et al., "Stereoelectronic control 1,3 of the diastereoselectivity in the photooxygenation (Schenck Ene Reaction) of an electron-poor allylic alchohol and its ethers", *J. Organic Chem.*, 63(2):226-227 (1998).
Burke and Pacofsky, "The ester enolate claisen rearrangement", *Tetra. Lett.*, 27(4):445-448 (1986).
Burke, et al., "Synthesis or ethisolide, isoavenaciolide and avenciolide", *J. Organic Chem.*, 57(8):2228-2235 (1992).
Cavallito and Haskell, "α-methylene butyrolactone from *Erythronium anerucanum*", *J. Am. Chem. Soc.*, 68(11):2332-2334 (1946).

Chen, et al., "Cytotoxic butanolides from *Litsea Akoensis*", *Phytochemistry*, 49(3):745-50 (1998).
Corbet and Benezra, "Allergenic alpha-methylene-gamma-lactones", *J. Organic Chem.*, 46(6):1141-1147 (1981).
Gelin and Chantegrel, "Synthesis of 3-Formyltetronic acid and enamine derivatives", *J. Heterocyclic Chem.*, 18:663-665 (1981).
Hall, et al., Anti-inflammatory activity of sesquiterpene lactones and related compounds, *J. Pharm. Sci.*, 68(5):537-42 (1979).
Hein, et al., "Bombardolides: new antifungal and antibacterial gamma-lactones from the coprophilous fungus *Bombardioidea anartia*", *J. Nat. Prod.*, 64(6):809-12 (2001).
Hidaka, et al., "Inhibition of polymorphonuclear leukocyte 5-lipoxygenase and platelet cyclooxygenase by alpha-(3,5-di-tert-butyl-4-hydroxybenzylidene)-gamma-butyrolacto ne (KME-4), a new anti-inflammatory drug", *Jpn. J. Pharmacol.*, 38(3):267-72 (1985).
Hutchinson, "A synthesis of tulipalin A and B and the acyiglucoside, tuliposide A, fungitoxic agents from *Tulipa gesneriana*. Carbon-13 nuclear magnetic resonance analysis of anomeric configuration in acylglucosides", *J. Organic Chem.*, 39(13):1854-8 (1974).
Kunes, et al., "Synthesis and antifungal activity evaluation of 3-hetaryl-2,5-dihydrofuran-2-ones", *Collect. Czech. Chem. Commun.*, 66:1809-1830.
Kwon, et al., "New cytotoxic butanolides from *Lindera obtusiloba* BLUME", *Chem. Pharm. Bull*. (Tokyo)., 48(5):614-6 (2000).
Murray and Norton, "The design and mechanism of palladium catalysts for synthesis of methylene lactones by cyclocarbonylation of acetylenic alcohols", *J. Amer. Chem. Soc.*, 101:4107-19 (1979).
Nishide, et al., "Total asymmetric syntheses of (+)-blastomycinone and related gamma-lactones", *Tetrahedron*, 50(28):8337-8338 (1994).
Paulitz, et al., "A novel antifungal furanone from *Pseudomonas aureofaciens*", *J. Chem. Eco.*, 26(6)1515-1524 (2000).
Pour, et al., "3-Phenyl-5-methyl-2H,5H-furan-2-ones: tuning antifungal activity by varying substituents on the phenyl ring", *Bioorg. Med. Chem. Lett.*, 10(16):1893-5 (2000).
Rezanka and Dembitsky, "gamma-Lactones from the soft corals *Sarcophyton trocheliophorum* and *Lithophyton arboreum*", *Tetrahedron*, 57(41):8743-8749 (2001).
Rollinson, et al., "The total synthesis of *Lauraceae* lactones", *J. Amer. Chem. Soc.*, 103(14):4114-4125 (1981).
Su and Tamm, "Synthesis studies towards Pseurotin A", *Helvet. Chim. Acta.*, 78:1278-1290 (1995).
Tsai, et al., "Cytotoxic butanolides from the stem bark of Formosan *Lindera communis*", *Planta Med*. , 67(9):865-7 (2001).
Viturro, et al., "Antifungal diastereomeric furanones from *Mutisia friesiana*: structural determination and conformational analysis", *Tetra. Asymm.*, 12(7):991-998 (2001).
Wong, *Chinese J. of Medic. Chem.*, 4(2): 137-149 (1994).
Zampella, et al., 'Amphiastemins: a new family of cytotoxic metabolites from the marine sponge *Plakortis quasiamphiaster*, *Tetrahedron*, 57(1):257-263 (2001).
Zapf, et al., "Incrusoporin, a new antibiotic from *Incrustoporia cameola*", *Acta. Chem. Scand.*, 49:233-34 (1995).
Chan, "Mechanisms of Renal Allograft Rejection," Transplant rejection and its Treatment (Tracy 12), Dec. 12, 2008.
Meyerkord, at al, "Loss of Hus 1 sensitizes cells to etoposide-induced apoptosis by regulating BH3-only proteins." *Oncogene*, 27(58): 7248-7259 (2008).
Strome, et al., "Heterozygous screen in *Saccharomyces cerevisiae* identifies dosage-sensitive genes that affect chromosome stability." *Genetics*, 178(3): 1193-1207 (2008).
Hopkins, et al., "Deletion of mouse rad9 causes abnormal cellular responses to DNA damage, genomic instability, and embryonic lethality." *Molecular and Cellular Biology*, 24(16) : 7235-7248 (2004).
Mon, et al., "Novel approaches to screen for anticancer drugs using *Saccharomyces cerevisiae*.", *Methods in Molecular Biology*, 223: 555-576 (2003).
Benezra, "Molecular recognition in allergic contact dermatitis to natural products", *Pure &Appl. Chem*, 62(7):1251-58 (1990).

* cited by examiner

SYNTHETIC LACTONE FORMULATIONS AND METHOD OF USE

CROSS REFERENCE TO RELATED APPLICATIONS

This application claims benefit under 35 U.S.C. §119 to U.S. Provisional Application No. 60/565,114, filed Apr. 23, 2004 and is also a continuation-in-part of U.S. Ser. No. 10/172,462, filed Jun. 12, 2002, now U.S. Pat. No. 6,900,242.

FIELD OF THE INVENTION

The present inventions are generally in the fields of pharmaceutically active lactones, their pharmaceutical formulations, and methods of use for treating pain.

BACKGROUND OF THE INVENTION

Despite the development of many different compounds which are useful in the treatment of pain, there remains a need for the development of new compounds which may be effective at lower dosages, are less habit-forming and have fewer side effects.

It is therefore an object of this invention to provide a new class of compounds that effectively treat pain.

It is another object of this invention to provide a new class of compounds that are effective at treating pain and are less habit-forming.

SUMMARY OF THE INVENTION

Dosage formulations containing an effective amount of a lactone compound of Formulae Ia, Ib, and Ic in a pharmaceutically acceptable carrier, to alleviate pain, have been developed. The lactone compound can be administered as the free base or a pharmaceutically acceptable salt or hydrate thereof. Studies have demonstrated that these compounds are useful as anti-bacterial, anti-fungal and anti-inflammatory agents, and for treating proliferation disorders such as melanoma, leukemia, breast cancer, lung cancer, ovarian cancer, colon cancer, esophagus cancer, liver cancer, and lymphatic cancer, as well as for treating pain associated with these disorders. Patients report that they are able to be removed from morphine when treated with the compounds disclosed herein, especially alpha-methylene-gamma-butyrolactone.

DETAILED DESCRIPTION OF THE INVENTION

I. Lactone Compositions

A. Lactones.

Lactones and their respective derivatives with a hydroxyl in the gamma position are disclosed. The lactones and the derivatives thereof can be synthesized or isolated from natural sources. In one embodiment, the lactones and the derivatives can be isolated by means of chromatographic methods, from a plant whose taxonomic scientific name is *Securidaca virgata*, which belongs to the botanical family Polygalaceae. As used herein, the term "lactones" encompasses any organic compounds having a five-member ring lactone structure in which the oxygen atom of the C=O group can be replaced by a sulfur atom or a nitrogen grouping. The term "derivatives" as used herein refers to any compounds that are made from the lactones by reacting the lactones with one or more chemical reagents. The term also refers to any products obtainable by ring opening of the lactones with an organic or inorganic nucleophilic agents to form, for example, an acid, ester, amide, or any other products thereof.

In one embodiment, the lactone has the following chemical structure:

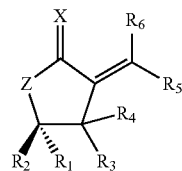

Formula Ia wherein $R_1$-$R_6$ taken independently are a hydrogen atom, a halogen atom, a hydroxyl group, or any other organic groupings containing any number of carbon atoms, preferably 1-8 carbon atoms, and optionally include a heteroatom such as oxygen, sulfur, or nitrogen grouping in linear, branched, or cyclic structural formats, representative $R_1$-$R_6$ groupings being H, alkyl, substituted alkyl, allyl, substituted allyl, alkenyl, substituted alkenyl, alkynyl, substituted alkynyl, phenyl, aryl, substituted aryl, heteroaryl, substituted heteroaryl, halo, hydroxyl, alkoxy, substituted alkoxy, alloxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_1$-$C_{20}$ cyclic, substituted $C_1$-$C_{20}$ cyclic, heterocyclic, substituted heterocyclic, aminoacid, peptide, or polypeptide group;

Z is a heteroatom such as oxygen, sulfur, or nitrogen grouping in linear, branched, or cyclic structural formats; and X is a heteroatom such as oxygen, sulfur, or nitrogen grouping in linear, branched, or cyclic structural formats.

In another embodiment, the lactone has the following chemical structure:

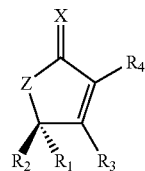

Formula Ib wherein $R_1$-$R_4$ taken independently may be a hydrogen atom, a halogen atom, a hydroxyl group, or any other organic groupings containing any number of carbon atoms, preferably 1-8 carbon atoms, and optionally include a heteroatom such as oxygen, sulfur, or nitrogen grouping in linear, branched, or cyclic structural formats, representative $R_1$-$R_4$ groupings being H, alkyl, substituted alkyl, allyl, substituted allyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, alloxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, C1-C20 cyclic, substituted $C_1$-$C_{20}$ cyclic, heterocyclic, substituted heterocyclic, aminoacid, peptide, or polypeptide group;

X is a heteroatom such as oxygen, sulfur, or nitrogen grouping in linear, branched, or cyclic structural formats; and Z is a heteroatom such as oxygen, sulfur, or nitrogen grouping in linear, branched, or cyclic structural formats.

In still another embodiment, the lactones having an alpha-methylene group can have the structure as show below:

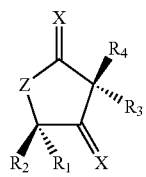

Formula Ic wherein $R_1$-$R_4$ taken independently may be a hydrogen atom, a halogen atom, a hydroxyl group, or any other organic groupings containing any number of carbon atoms, preferably 1-8 carbon atoms, and optionally include a heteroatom such as oxygen, sulfur, or nitrogen grouping in linear, branched, or cyclic structural formats, representative $R_1$-$R_4$ groupings being alkyl, allyl, substituted alkyl, alkenyl, allyl, substituted allyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, alloxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, C1-C20 cyclic, substituted $C_1$-$C_{20}$ cyclic, heterocyclic, substituted heterocyclic, aminoacid, peptide, or polypeptide group;

Z is a heteroatom such as oxygen, sulfur, or nitrogen grouping in linear, branched, or cyclic structural formats; and X is a heteroatom such as oxygen, sulfur, or nitrogen grouping in linear, branched, or cyclic structural formats.

In a preferred embodiment, the lactone is α-methylene-γ-butyrolactone, also known as Securolide, which has the structure shown below:

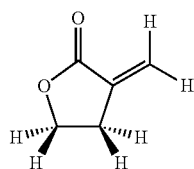

The pharmaceutically acceptable acid addition salts of compounds of the formula Ia, Ib, or Ic, may be prepared in a conventional manner by treating a solution or suspension of the free base of the formula 1 with about one chemical equivalent of a pharmaceutically acceptable acid. Conventional concentration and recrystallization techniques can be employed to isolate the salt.

The pharmaceutically acceptable base addition salts of compounds of formula 1 containing an acid group may be prepared in a conventional manner from the acid, e.g. by reaction with about one chemical equivalent of a base.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, tolunesulfonic, naphthalenesulfonic, methanesulfonic, ethane disulfonic, oxalic, and isethionic.

The pharmaceutically acceptable salts of the compounds can be synthesized from the parent compound, which contains a basic or acidic moiety, by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Remington's Pharmaceutical Sciences, 20th ed., Lippincott Williams & Wilkins, Baltimore, Md., 2000, p. 704.

B. Excipients

The lactone and functional derivatives can be formulated using standard techniques for enteral, parenteral, topical administration (see, for example, Encyclopedia of Controlled Drug Delivery, Edith Mathiowitz, Ed., John Wiley & Sons, Inc., New York, 1999). Effective dosages can be determined based on the in vitro assays known to those skilled in the art, such as the assays described in the examples.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

Suitable pharmaceutically acceptable vehicles for parenteral delivery include sterile saline, phosphate buffered saline, apyrogenic sterile vehicle, and standard microparticulate formulations for injection, including polymeric microspheres, microcapsules, liposomes, and emulsions. These can include degradable polymers such as polylactic acid and polyglycolic acid, and copolymers thereof, polyanhydrides, polyorthoesters, and polyhydroxyalkanoates.

Suitable pharmaceutically acceptable carriers include talc, gum Arabic, lactose, starch, magnesium stearate, cocoa butter, aqueous or non-aqueous vehicles, fatty substances of animal or vegetable origin, paraffin derivatives, glycols, various wetting, dispersing or emulsifying agents and preservatives.

For injection, the lactones will typically be formulated as solutions or suspensions in a liquid carrier.

For topical delivery, the lactone may be formulated in an ointment, creams, lotion, gel, spray, or controlled or sustained release formulation (such as a transdermal patch).

For enteral delivery, the lactone may be formulated in a tablet, capsule, granule, suppository, suspension or solution, dissolved or encapsulated in an excipient such as a sugar like lactose, inert compound such as magnesium stearate, paraffin derivatives, glycols or gum arabic. The formulations may further include dyes, flavorings, preservatives, dispersing or emulsifying agents, or materials modifying release or stability properties of the formulations.

Formulations are prepared using a pharmaceutically acceptable "carrier" composed of materials that are considered safe and effective and may be administered to an individual without causing undesirable biological side effects or unwanted interactions. The "carrier" is all components present in the pharmaceutical formulation other than the active ingredient or ingredients. The term "carrier" includes but is not limited to diluents, binders, lubricants, desintegrators, fillers, and coating compositions.

"Carrier" also includes all components of the coating composition which may include plasticizers, pigments, colorants, stabilizing agents, and glidants. The delayed release dosage formulations may be prepared as described in references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", $6^{th}$ Edition, Ansel et. al., (Media, Pa.: Williams and Wilkins, 1995) which provides information on carriers, materials, equipment and process for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name Eudragit® (Roth Pharma, Westerstadt, Germany), Zein, shellac, and polysaccharides.

Additionally, the coating material may contain conventional carriers such as plasticizers, pigments, colorants, glidants, stabilization agents, pore formers and surfactants.

Optional pharmaceutically acceptable excipients present in the drug-containing tablets, beads, granules or particles include, but are not limited to, diluents, binders, lubricants, disintegrants, colorants, stabilizers, and surfactants.

Diluents, also termed "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powder sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydorxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone XL from GAF Chemical Corp).

Stabilizers are used to inhibit or retard drug decomposition reactions which include, by way of example, oxidative reactions.

Surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, and ammonium salts of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-.beta.-alanine, sodium N-lauryl-.beta.-iminodipropionate, myristoamphoacetate, lauryl betaine and lauryl sulfobetaine.

If desired, the tablets, beads granules or particles may also contain minor amount of nontoxic auxiliary substances such as wetting or emulsifying agents, dyes, pH buffering agents, and preservatives.

The amount of active agent released in each dose will be a therapeutically effective amount.

The active compound may be used in combination with a second pharmaceutically acceptable antimicrobial agent such as nitroimidazole antibiotics, e.g. tinidazole and metronidazole; tetracyclines, e.g. tetracycline, doxycycline and minocycline; penicillins, e.g. amoxicillin and meziocillin; cephalosporins, e.g. cefaclor, cefadroxil, cephadrine, cefuroxime, cefuroxime axetil, cephalexin, cefpodoxime proxetil, ceftazidime and cefatriaxone; carbapenems, e.g. imipenem and meropenem; aminoglycosides, e.g. paromomycin; macrolide antibiotics, e.g. erythromycin, clarithromycin and azithromycin; lincosamide antibiotics, e.g. clindamycin; rifamycins, e.g. rifampicin; and nitrofurantoin.

Combinations of the compounds with a pharmaceutical acid-lowering agent may used in the treatment of acid-related disorders, such as acid pump inhibitors, e.g., omeprazole and lansoprazole, or $H_2$ antagonists, e.g., ranitidine, cimetidine, and famotidine.

II. Synthesis of Lactones

The synthesis of the lactones of formulae Ia, Ib, and Ic involves: a) forming an intermediate or precursor having the lactone structure, and b) reacting the intermediate with one or more appropriate chemical agents to form the lactones of formulae Ia, Ib, and Ic.

In one embodiment, the method involves: a) providing a precursor having the following structure:

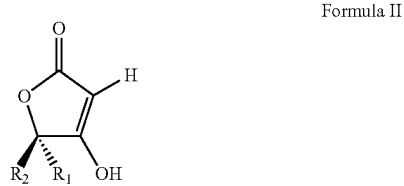

Formula II and b) reacting the precursor with one or more appropriate chemical reagents to provide a lactone product of formula Ia, Ib, or Ic (Scheme 1).

As shown by Scheme 1, an acetylene can react with an aldehyde in the presence of a phosphine, $[CH_3(CH_2)_3]_3P$, to form compound A, which undergoes a ring-rearrangement reaction to form compound B in enolic form. Enolic compound B is in equilibrium with its ketone form, compound C. Reaction of either B or C in the presence of a base such as butyl lithium, sodium carbonate, sodium hydroxide, or sodium methoxide or ethoxide to form compound E (Formula Ic) or F (Formula Ib). In the alternative, the enolic compound B can be subjected to reduction reaction with $NaBH_4$ to form saturated compound D. Compound D undergoes condensation reaction with $HCO_2Et$ to form an exocyclic enolate, compound G, which is then reduced by formyl aldehyde to form compound H. Compound H can be readily derivatized to form compound I (Formula Ia) using, for example, an alkyl halide in the presence of a base such as sodium carbonate, sodium hydroxide, or sodium methoxide or ethoxide.

More functionalized lactones can be prepared by readily available synthetic method in the art (see, for example,

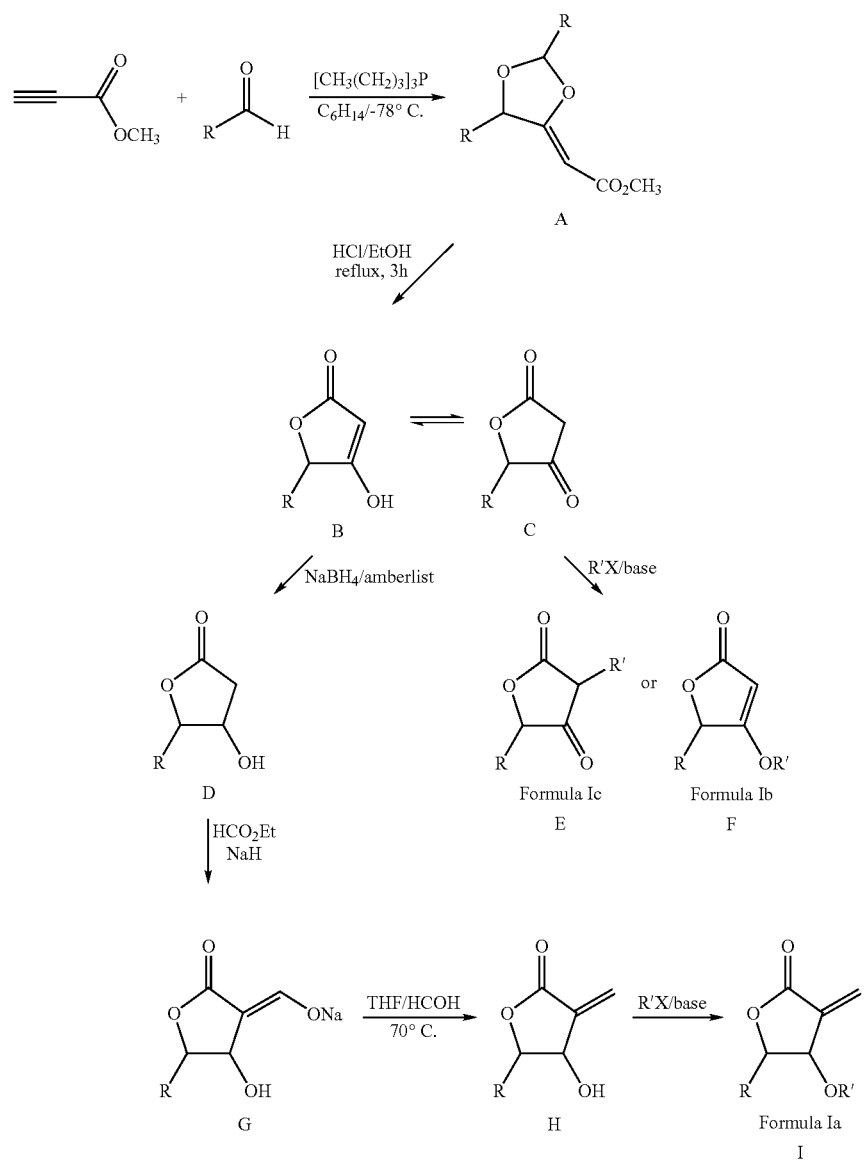

March, "Advanced Organic Chemistry," 4th Edition, 1992, Wiley-Interscience Publication, New York).

The pharmaceutically acceptable salts of the lactone compounds of the Formulae Ia-c, if in the form of an acid or a base such as an amine, can be prepared in a conventional manner by treating a solution or suspension of the compound of Formulae Ia-c with about one chemical equivalent of a pharmaceutically acceptable base or acid. Conventional concentration and recrystallization techniques are employed in isolating the salt.

III. Methods of Treatment

A. Disorders to be Treated

The lactones are useful to treat pain, particularly pain associated with disorders including cancers. Representative types of cancers include melanoma, leukemia, breast cancer, lung cancer, ovarian cancer, colon cancer, esophagus cancer, liver cancer, and lymphatic cancer.

The lactones can be formulated into analgesic compositions. Analgesic compositions are comprised of a therapeutically effective amount of a compound of formulae Ia, Ib, or Ic or a salt thereof and an inert pharmaceutical carrier to alleviate pain.

B. Dosages

The effective amount will be determined based on the pain to be treated, the mode of administration and the formulation. Effective dosages can be routinely determined based on the effective dosages determined using in vivo assays such as those described in the examples.

The preferred compound is alpha-methylene-gamma-butyrolactone, also referred to as 4,5-dihydro-3-methylene-2 [3H]furanone, "Securolide" or "LMSV-6", for the treatment of pain. Typical doses for cancer patients for relief of pain are 60 mg/day given once or twice daily intramuscularly. The $LD_{50}$ in rabbits for the compounds disclosed is 225 mg/kg. Typical maximum dosages for humans is 60% of the $LD_{50}$. Toxicity in humans occurs between about 300 and 400 mg/day.

The compounds can be administered to humans for the treatment of pain associated with disorders such as cancer by either the oral or parenteral routes and may be administered orally at dosage levels of about 0.1 to about 100 mg/kg, advantageously about 0.5 to 60 mg/kg/day given once or twice a day. For intramuscularly or intravenous administration, dose levels are about 0.1 to about 100 mg/kg/day, preferably about 0.5 to about 60 mg/kg/day. While intramuscular administration may be a single dose or up to 4 divided doses, intravenous administration can include a continuous drip.

C. Mode of Administration

The lactone composition can be administered by any standard route, either systemically, topically or locally. Preferred routes of administration are by injection, orally using an enteric coating, or topically in ointment form. The mode of administration will vary with the type of pain to be alleviated.

The compounds may be administered alone, but will generally be administered in admixture with a pharmaceutical carrier selected with regard to the intended route of administration and standard pharmaceutical practice. For example, they can be administered orally or in the form of tablets containing such excipients as starch or lactose, or in capsules either alone or in admixture with excipients, or in the form of elixirs or suspensions containing flavoring or coloring agents. In the case of humans, the compounds may be administered as syrup or enteric coated tablets. In addition, they can be injected parenterally, for example, intramuscularly, intravenously or subcutaneously. For parenteral administration, they are best used in the form of a sterile aqueous solution which can contain other solutes, for example, sufficient salt or glucose to make the solution isotonic.

A preferred method of intramuscular administration of the alpha-methylene-gamma-butyrolactone is via an oil-based carrier, such as Cremophor (the same carrier typically used to administer taxol). A more preferred method is via an injectable aqueous solution. For topical administration, the compounds can be administered as a cream with a dose of 60 mg/12 g of an emulsion such as Vaseline®. Variations in dosage and formulation will result based on the weight and condition of the subject being treated and the particular route of administration chosen as will be known to those skilled in the art.

The present invention will be further understood by reference to following non-limiting examples.

Example 1

Study of Adverse Reactions to LMSV-6 in Healthy Volunteers

Methods

Nineteen healthy volunteers participated in the study. The age of the participants was between 21 and 40 years with an average of 30.5±7.2 years. The weight was between 150 and 190 pounds with a median of 163.2±14.3 pounds and the height was 1.8 to 2.1 meters with an average of 1.9±0.1 meters. The subjects were selected at random in agreement with the national and international criteria and norms established for investigations with human beings.

The state of health of the participants was established using several clinical evaluations, laboratory tests, electrocardiographs and thoracic radiographs. The functionality of the liver and the renal systems was verified by chemical-enzymatic studies. Likewise, for each participant, tests of blood chemistry, pathology and urinalysis were carried out. For the female participants, the absence of pregnancy and/or lactation was verified by means of laboratory tests and gynecological evaluation.

Participants were divided into three groups selected at random (n=6):

Group I (placebo) received 2.0 ml of saline solution ($ClNa^+$, 0.9%),

Group II, received 60 mg of LMSV-6 intramuscularly, and Group III (n=7) received 100 mg of LMSV-6 intramuscularly. The participants underwent several tests used to establish the basal values of the objective parameters of the analysis, which included:

Lab Studies: hemogram, blood chemistry, urinalysis and coproanalysis

Cardiovascular Function: arterial tension (TA), cardiac rhythm (RC), cardiac frequency (FC) and radial pulse (PR)

Pulmonary Functions: pulmonary respiration (VP) and respiratory frequency (FR)

Renal Function: urinary volume and urinary frequency (FU)

Sensory System: hearing, vision, smell, taste and sensory reflexes

Skin and/or Teguments: sensitivity, skin texture, temperature and musculo-skeletal tone Neurovegetative Functions: salivary gland and sweat gland activities, gastrointestinal mortality and visceral reflexes Hypersensitivity Reactions: local sensitivity and systemic sensitivity.

The evaluations were taken at the following time intervals: Time 0.0, 5.0, 15.0, 20.0, 30.0 and 45.0 min.; 1.0 h., 1.5, 2.0, 3.0, 4.0, 6.0, 8.0, 12.0, 24.0, 36.0 and 48.0 hours.

Results

The reports of the laboratory tests and special exams performed to verify the state of health of the participants showed the values were maintained within the basal levels and there was no observation of any difference with respect to the group that received the placebo.

The results of the laboratory tests performed dealing with the urinary functions and the microbiological pattern found the values to be within the reference values for the utilized methods. Likewise, the results of the copra analysis also showed no pathological change.

The individual values and averages±standard deviation per group of participants before and during the trials were measured to determine the adverse reaction and margin of tolerance to LMSV-6 with respect to cardiovascular parameters including arterial tension (TA), cardiac frequency (FC), radial pulse (PR) and cardiac rhythm (RC). For healthy volunteers, which received 60 and 100 mg of LMSV-6 and 2 ml of 0.9% sodium chloride as a placebo, the results show that in relation to the basal values and those of the placebo control group, the levels of TA, FC, PR and RC did not change with the treatment. Likewise, there was no variation in the electrocardiograph pattern between the basal conditions and after the study.

The individual values and the averages±standard deviations per group involved in the evaluation of the effects of LMSV with respect to the respiratory functions in healthy volunteers were also measured. The results demonstrate that in relation to the basal values and those of the placebo control group, the treatment in the tested dosages did not alter the respiratory mechanics and dynamics of the participants. The respiratory frequency (FR) was maintained in a range of 18 to 20 respirations per minute during the entire test.

According to that which was observed in the basal conditions and in the placebo group, none of the parameters evaluated dealing with the respiratory dynamic, inspiration, aspiration, tracheal respiration, bronchial respiration and thoracic-pulmonary distension and the superior and inferior airflow, suffered any alteration.

The evaluation of the effects of LMSV-6 with respect to the renal function parameters showed that the values of urinary frequency in individuals of the control group and those who were treated were maintained within a range, without much significant variation, of 3.1±0.7 to 3.3±1.5 times in a period of 12 hours of direct observation. Likewise, the average urinary volume in the same period was between 434.2±213.2, 489.2±94.3 and 394.3±103.9 ml in the placebo groups and the groups which received 60 and 100 mg of LMSV-6, respectively. This demonstrates that the treatment did not affect the fundamental renal functions.

The data of the effect of LMSV-6 on the mental state and sensory acuteness: auditory, visual, olfactory and taste discrimination indicate that the treatment did not provoke any alteration in any of the functions or analyzed parameters. Likewise, there was not any alteration in the superficial and osteotendinous reflexes.

The data of the evaluation of the effects of LMSV-6 on cutaneous sensitivity and temperature indicate that the treatment did not provoke any change in the cutaneous sensitivity, or in the temperature of the participants. Likewise, there is no evidence of any alteration in the musculo-skeletal tone of any of the participants of the control groups or the treated groups.

The treatment did not produce any alteration in the texture or moisture of the skin in any of the participants in the study, and there was no change observed in the characteristics of the oral and nasal mucosa due to a treatment effect.

The data dealing with the evaluation of allergic effects (reactivity), both local and systemic, indicate that there was not any manifestation of allergic reactions in any of the participants.

The data of the evaluation and effects of LMSV-6 at a neurovegetative level (glandular and visceral) show that in the ranges of studied dosages (60 and 100 mg), there is no evidence of any manifestation of neurovegetative alteration at the gastrointestinal visceral level, genito-urinary level, larynx-opthalmic glands, nor cardiotonic effect; which is to say, there is no alteration at the level of the exocrine and endocrine glands.

The results of the present study affirm that LMSV-6 possesses an ample margin of tolerance and that the maximum dosage tested (100 mg) was well tolerated by all participants. Likewise, there is no evidence, sign or symptom of adverse reactions in any participants involved in the study.

Example 2

Administration to Cancer Patients

Securolide was administered to a number of cancer patients for the treatment of cancer. The dosage was 60 mg/once or twice daily. The dosage was given in an oil base or in Cremophor by intramuscular injection.

An unanticipated outcome of the study was that patients who were on morphine for control of pain were able to be removed from the morphine and were free from pain associated with the cancer.

The invention claimed is:

1. A method of treating pain in a patient having a proliferation disorder comprising administering to an animal an effective amount of a composition comprising a compound or a pharmaceutically acceptable salt in a pharmaceutically acceptable carrier, to alleviate pain associated with cancer, wherein the compound has the following structure:

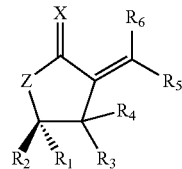

Formula Ia wherein $R_1$-$R_6$ taken independently are a hydrogen atom or a group or grouping selected from the group consisting of alkyl, substituted alkyl, ally, substituted allyl, alkenyl, substituted alkenyl, alkynyl, substituted alkynyl, phenyl, aryl, substituted aryl, heteroaryl, substituted heteroaryl, halo, hydroxyl, alkoxy, substituted alkoxy, alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, C1-C20 cyclic, substituted C1-C20 cyclic, heterocyclic, substituted heterocyclic, aminoacid, peptide, and polypeptide groups;

Z is a heteroatom selected from the group consisting of oxygen, sulfur, and nitrogen groupings in linear, branched, or cyclic structural formats; and X is a heteroatom selected from the group consisting of oxygen, sulfur, and nitrogen groupings in linear, branched, or cyclic structural formats.

2. The method of claim 1 wherein the compound is α-methylene-γ-butyrolactone (Securolide).

3. The method of claim 1 wherein the proliferation disorder is a cancer selected from the group consisting of melanoma, leukemia, breast cancer, lung cancer, ovarian cancer, colon cancer, esophagus cancer, liver cancer, and lymphatic cancer.

4. The method of claim 1 wherein the dosage of the compound is equivalent to 60 to 120 mg/day given intramuscularly.

5. The method of claim 1 wherein the dosage is up to 400 mg/day.

6. The method of claim 1 wherein the compound is administered in an ointment or cream applied to the skin or mucosal surface.

7. The method of claim 1 wherein the compound is administered by injection.

8. The method of claim 7 wherein the compound is in an oil or cremophor based carrier.

9. The method of claim 1 wherein the compound is enteric coated for oral administration.

10. The method of claim 1 wherein the compound is in a syrup.

* * * * *